United States Patent
Roberts et al.

(10) Patent No.: US 9,854,743 B2
(45) Date of Patent: Jan. 2, 2018

(54) DEVICE AND METHOD FOR MEASURING THE MOISTURE OF HAY IN THE PRE-COMPRESSION CHAMBER OF A RECTANGULAR BALER

(71) Applicants: Jeffrey S. Roberts, Hudson, WI (US); Ryan P. Johnson, Woodbury, MN (US)

(72) Inventors: Jeffrey S. Roberts, Hudson, WI (US); Ryan P. Johnson, Woodbury, MN (US)

(73) Assignee: Harvest Tec, Inc., Hudson, WI (US)

( * ) Notice: Subject to any disclaimer, the term of this patent is extended or adjusted under 35 U.S.C. 154(b) by 1097 days.

(21) Appl. No.: 13/906,971

(22) Filed: May 31, 2013

(65) Prior Publication Data
US 2013/0319263 A1    Dec. 5, 2013

Related U.S. Application Data

(60) Provisional application No. 61/653,924, filed on May 31, 2012.

(51) Int. Cl.
| A01F 15/08 | (2006.01) |
| G01N 27/04 | (2006.01) |
| A01F 15/10 | (2006.01) |

(52) U.S. Cl.
CPC .......... *A01F 15/0825* (2013.01); *A01F 15/08* (2013.01); *A01F 15/101* (2013.01); *G01N 27/048* (2013.01); *A01F 15/0816* (2013.01); *A01F 2015/102* (2013.01)

(58) Field of Classification Search
CPC .... A01F 15/08; A01F 15/101; A01F 15/0816; A01F 2015/102; A01F 15/0825; G01N 27/048
USPC .............................. 100/45, 179, 188 R, 190
See application file for complete search history.

(56) References Cited

U.S. PATENT DOCUMENTS

| 3,330,035 | A | * | 7/1967 | Pradenas | ............... | E01C 11/265 |
| | | | | | | 219/544 |
| 4,812,741 | A | * | 3/1989 | Stowell | ................ | G01N 27/048 |
| | | | | | | 324/695 |
| 4,918,910 | A | * | 4/1990 | Sheehan | .............. | A01F 15/0816 |
| | | | | | | 100/45 |
| 4,929,904 | A | * | 5/1990 | Bohman | .............. | A01D 89/006 |
| | | | | | | 324/694 |
| 6,007,697 | A | * | 12/1999 | Yagi | .................... | G01N 27/4175 |
| | | | | | | 204/402 |
| 7,340,996 | B1 | * | 3/2008 | Viaud | ..................... | A01F 15/08 |
| | | | | | | 100/87 |

(Continued)

FOREIGN PATENT DOCUMENTS

JP    2000241366 A   *   9/2000

*Primary Examiner* — Jimmy T Nguyen
(74) *Attorney, Agent, or Firm* — Skinner and Associates; Joel Skinner

(57) ABSTRACT

A system and method for measuring the moisture of a harvested crop, such as hay, in the pre-compression chamber of a harvesting apparatus, such as a large square hay baler. Measurement at this time provides a highly accurate and reliable moisture reading. The apparatus disclosed includes two or more sensors disposed at separate positions in the pre-compression chamber. The sensors sense electrical conductivity or RF wave transmission through the hay in the pre-compression chamber.

12 Claims, 13 Drawing Sheets

(56) References Cited

U.S. PATENT DOCUMENTS

| | | | |
|---|---|---|---|
| 2007/0175341 A1* | 8/2007 | Roberts | A01F 15/08 100/102 |
| 2010/0242749 A1* | 9/2010 | Demulder | A01F 15/042 100/179 |
| 2012/0000377 A1* | 1/2012 | Verhaeghe | A01F 15/0825 100/45 |
| 2012/0103205 A1* | 5/2012 | Kraus | A01F 15/08 100/2 |
| 2012/0240797 A1* | 9/2012 | Verhaeghe | A01F 15/0825 100/43 |

* cited by examiner

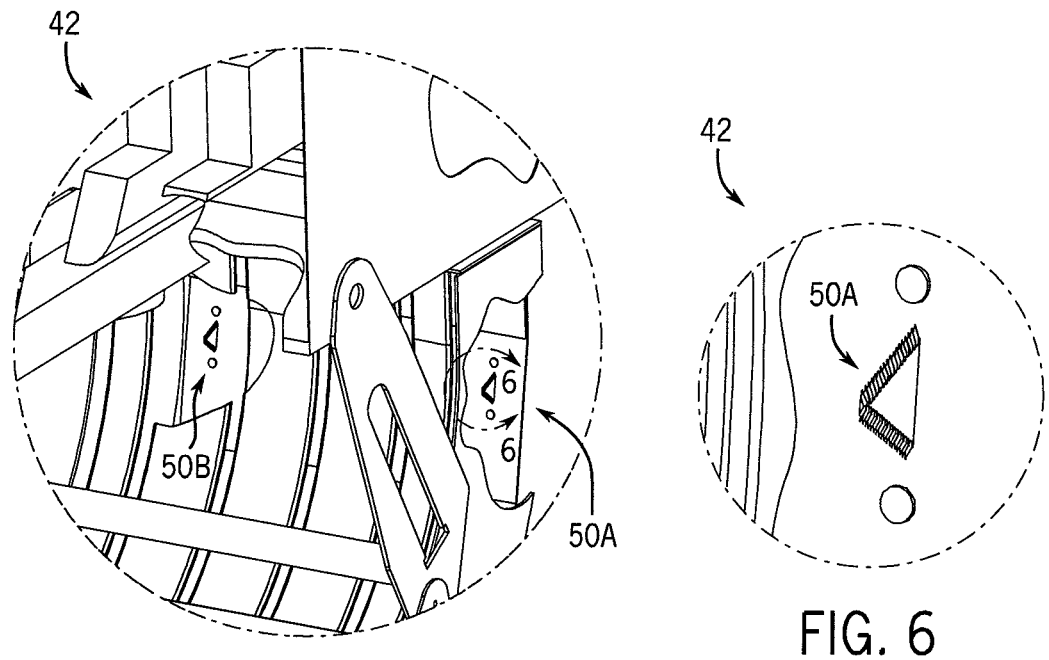
FIG. 5
FIG. 6
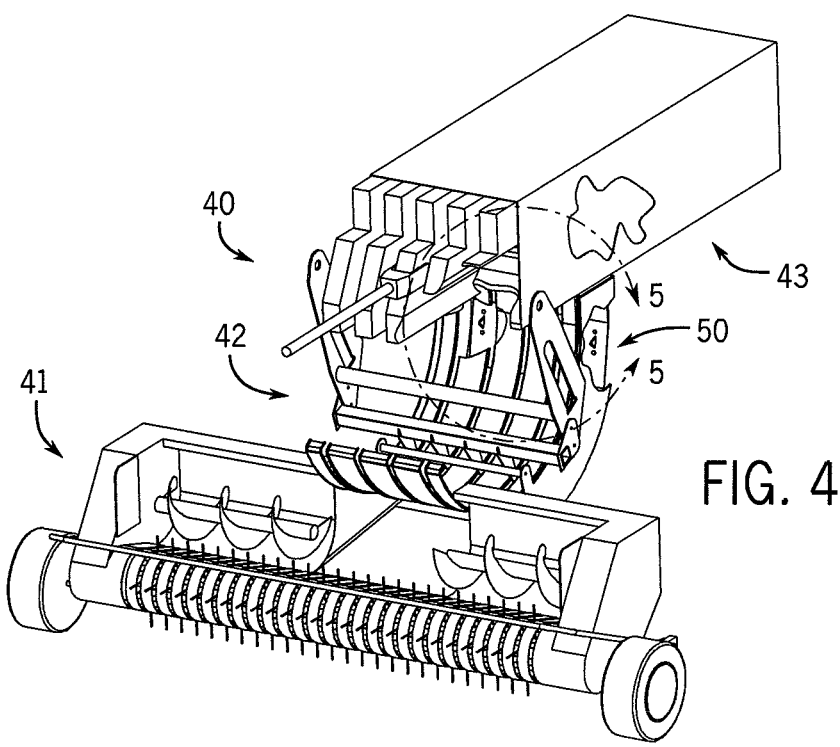
FIG. 4

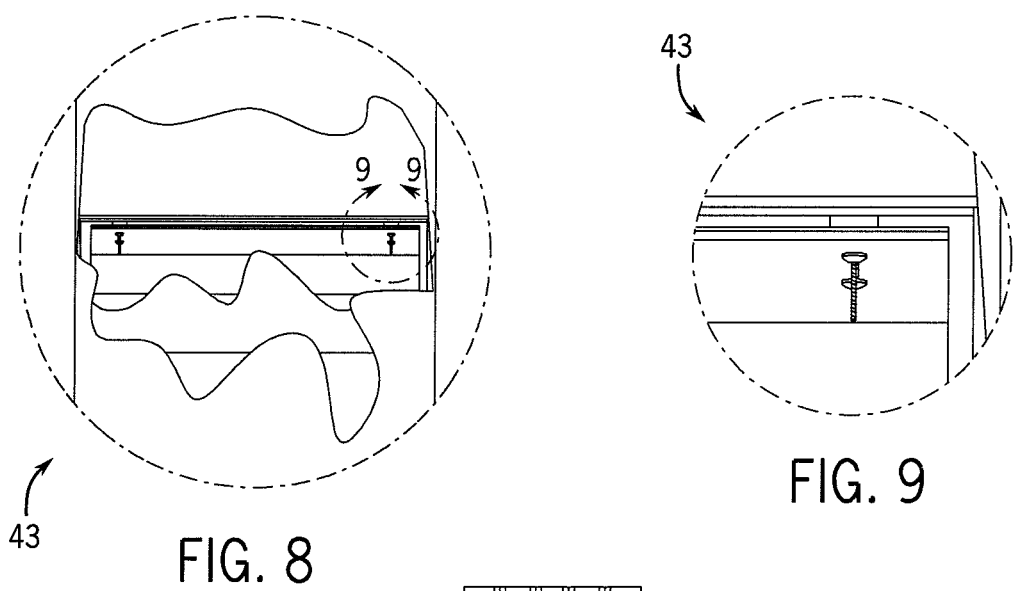
FIG. 8
FIG. 9
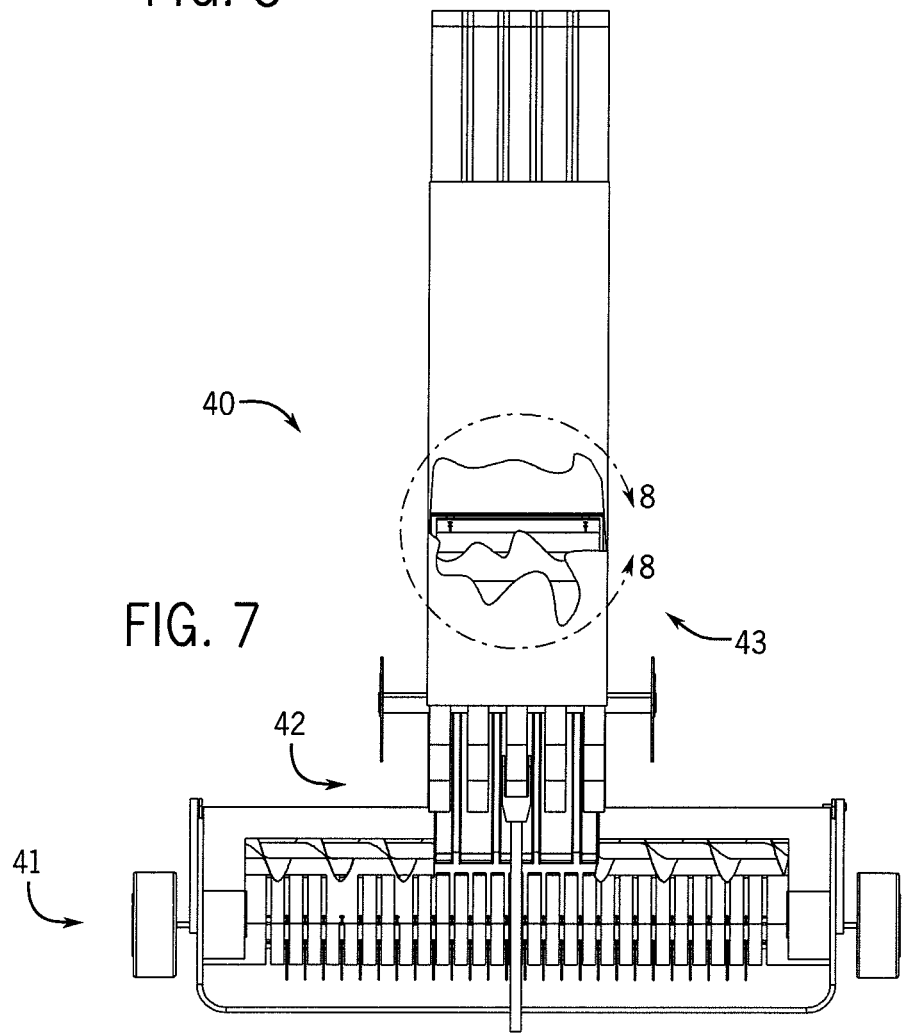
FIG. 7

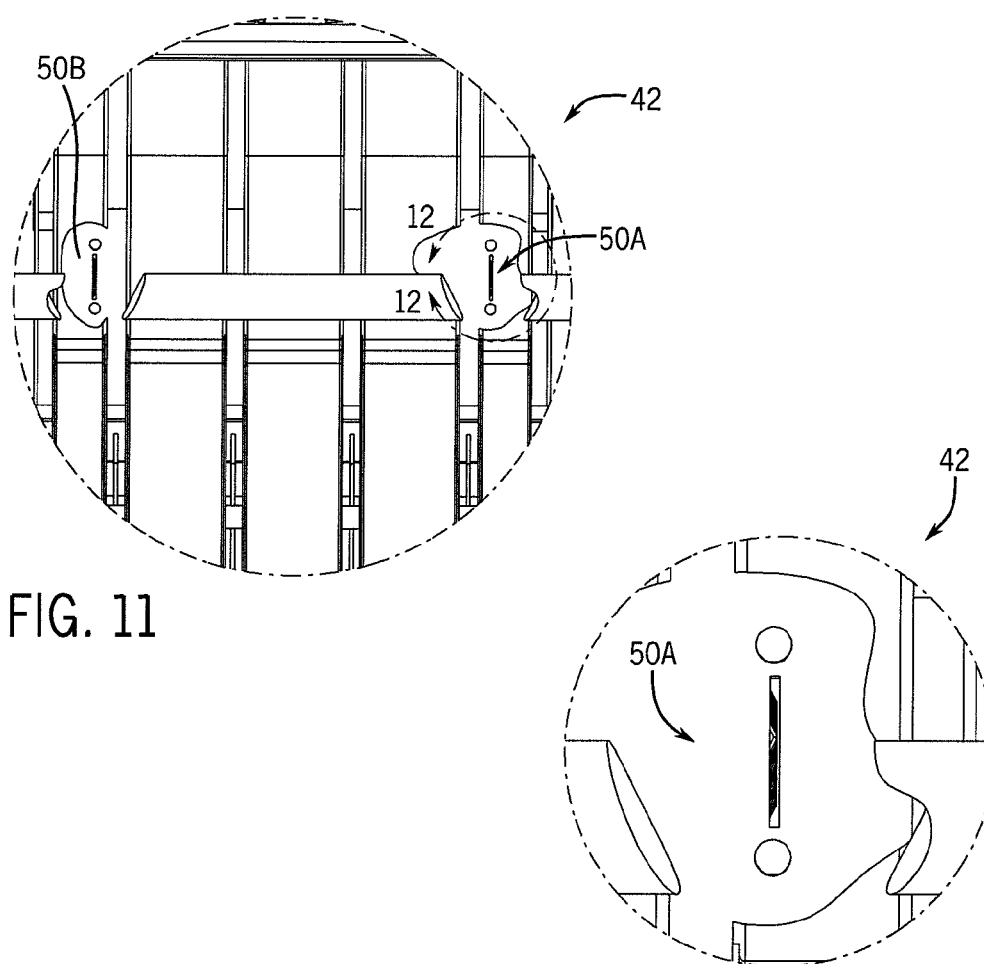
FIG. 11
FIG. 12
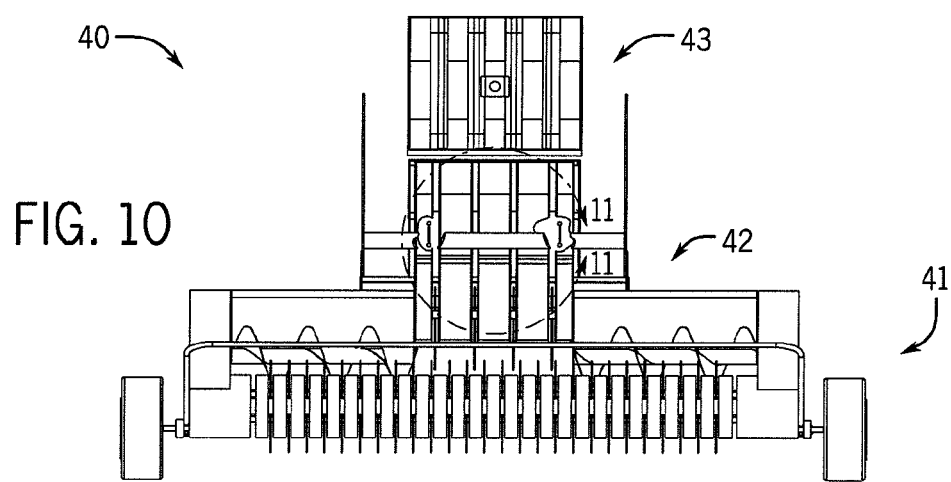
FIG. 10

DEVICE AND METHOD FOR MEASURING THE MOISTURE OF HAY IN THE PRE-COMPRESSION CHAMBER OF A RECTANGULAR BALER

CROSS REFERENCE TO RELATED APPLICATION

This application claims the benefit under 35 U.S.C. §119(e) of U.S. Provisional Patent Application Ser. No. 61/653,924, filed May 31, 2012, which is hereby incorporated by reference.

37C.F.R. §1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to crop harvesting systems, apparatus and methods. Particularly, the invention relates to hay harvesting systems, apparatus and methods. The present invention is most particularly suitable for use in and for large rectangular (often called "square") hay balers.

2. Background Information

Harvesting baled hay at the correct moisture is difficult due to the variation in moisture of the crop as it is close to the target moisture for baling of 13% to 16%. Hay harvested below that level is too dry leading to excess losses due to shatter and hay harvested above that level is too wet leading to spoilage of the crop in storage. Due to the variation, moisture monitoring devices mounted in hay baling implements have become popular with the producers of hay, giving them continuous information on the moisture of the crop as the hay is being baled.

Implement-mounted moisture monitors include electrical current based devices and radio wave based devices. Use of these monitors has become common-place in hay baling. Moisture in a bale is the most important factor in the transmission of electrical signals through the bale. Current based moisture sensors estimate hay moisture by sensing electrical transmission of current through a bale. In such devices, one positive polarity sensor is located opposite a negative polarity sensor and the continuity between the sensors is measured and associated with the moisture in the hay bale. In radio wave transmission devices, one sensor emits a radio wave signal through the bale while a second sensor receives the radio wave signal and the higher the moisture of the bale, the stronger the transmission of the radio wave signal received by the second sensor. If all other variables affecting the transmission of current or radio signals are unchanged, a change in signal transmission will result in good estimate in the level of moisture in the hay bale.

A second significant factor affecting the transmission of signals through the bale being tested during baling is the density of the bale at the point at which signal transmission is measured. The higher the density, the more transmission of the signal will occur. The density of the bale within areas of the bale can vary from 1 pound per cubic foot (loose hay) to 30 pounds per cubic foot (tightly compacted hay). To effectively monitor changes in moisture, sensors need to be located in a position where the density of the bale is somewhat consistent. A common location on the baler where density of the bale is consistent is in the baler's "chamber" (or "bale chamber") where hay density is controlled by a combination of a plunger compressing the hay against restrictors to the flow of hay. Locating the sensors in the chamber has drawbacks however. One drawback is the delay that is required for the crop being baled to move through the baler to the chamber, which is located at the rear of the baler. Another drawback is the limitation of sensing all the crop being baled as the sensors are placed in one area of the bale and moisture in other areas can remain unseen. In cases where the hay moisture makes a rapid change over a relatively small area of the field being harvested, the bales could have significantly different moisture in different areas of the bale. If the operator of the baler is relying on the moisture being monitored by the device to determine if the hay is too dry or too wet to continue baling, the lag in readings will lead to a significant amount of hay being harvested outside the desired range before balling is suspended. In the case of preservative application systems that are controlled by input from moisture-sensing devices to regulate the amount of preservative based on the moisture of the hay it is applied to, the preservative application which has to be done to loose hay on the front of the baler to assure adequate coverage, application does not match up to the moisture in the location of application. The sensing of moisture in closer proximity to the point of application would have the advantage of closely matching preservative application to moisture content. However, density of the hay being baled has variability in areas of the baler which are located toward the front of the baler, anterior to or forward of the bale chamber, closer to the field.

The transmission of the electrical signal between sensors is also typically influenced by electrical transmission through adjacent metal parts. Such parts typically have much higher properties of transmission than hay. When the sensors are located within a baler's chamber, if all parts of the bale are not isolated from contact with metal, conductivity between the sensors can follow the pathway from the sending sensor to the closest metal surface, through the metal surface closest to the receiving sensor. In this manner, only the moisture of the hay between metal surfaces and the sensors will change the conductivity between the sensors eliminating any influence in electrical transmission from the moisture in other parts of the bale. With all types of sensors commonly in use, the close proximity of the sensors to metal results in a small amount of hay being tested for moisture. And, inside the chamber, there is a significant amount of metal surface that would have to be lined with a non-conductive material to eliminate contact between the bale and metal.

One type of rectangular baler currently in use is commonly called a "large square baler." These are typically between twenty-four and fifty inches (24-50 in.) wide, twenty-four and fifty inches high (24-60 in.) and sixty inches and one-hundred inches (60-100 in.) long. Recent developments in the design of large square balers have added a "pre-compression chamber" to the implement that leads to the formation of a more uniform bale. In the feeding of the hay, material is held by a door or other types of flow restrictors in a pre-compression chamber just after it is picked up from the field. When the density of the hay in this chamber reaches a certain point, the door opens allowing the hay to move into the baler's chamber, forming a more consistent bale than if it moved into the chamber without pre-compression. The tension on the door is controlled by a mechanical device such as a spring and when a set tension is reached the door trips allowing the hay to move into the chamber.

In the present invention, the consistent state of hay density occurring momentarily in the pre-compression chamber just before the door opens is utilized to attain a more timely reading of moisture. Sensing moisture in this area also allows for the hay being tested to be isolated from metal parts on the baler due to the containment of the hay in this small area making it practical to line the area of the pre-compression chamber with non-conductive material.

Existing technology in this field is believed to have significant limitations and shortcomings.

All US patents and patent applications, and all other published documents mentioned anywhere in this application are incorporated by reference in their entirety.

BRIEF SUMMARY OF THE INVENTION

The present invention provides a hay harvesting apparatus and methods which are practical, reliable, accurate and efficient, and which are believed to constitute an improvement over the background technology. The invention provides an improved large square baler that has optimized moisture measurement capability. The invention also provides a moisture measurement system that can be implemented in or added to an existing large square baler.

The device and method preferably involve two or more electrical sensors mounted in the pre-compression chamber of a large square hay baler. Electrical transmission is measured between the sensors just prior to and just after the door or other type of flow restrictor that keep the hay in the pre-compression chamber is opened so that the electrical transmission is measured thru the bale that has a more consistent density than the bale at other points in the baler's cycle. The value of the electrical transmission is assigned to a moisture value of the hay being baled.

In one aspect, the invention provides a crop baler of the type having a pre-compression chamber, comprising: at least two sensors disposed at separate predetermined positions in the pre-compression chamber, the sensors sensing an a parameter associated with moisture of crop disposed in the pre-compression chamber at a predetermined time.

In another aspect, the invention provides a hay moisture measurement system for use with a hay baler of the type having a pre-compression chamber, comprising: at least two sensors disposed at separate predetermined positions in the pre-compression chamber, the sensors sensing an a parameter associated with moisture of hay disposed in the pre-compression chamber at a predetermined time.

In yet another aspect, the invention provides an improved hay baler of the type having a pre-compression chamber, the improvement comprising: at least two sensors disposed at separate predetermined positions in the pre-compression chamber, the sensors sensing an a parameter associated with moisture of hay disposed in the pre-compression chamber at a predetermined time.

The present invention is believed to involve novel elements, combined in novel ways to yield more than predictable results. The problems solved by the invention were not fully recognized in the prior art.

The aspects, features, advantages, benefits and objects of the invention will become clear to those skilled in the art by reference to the following description, and drawings.

BRIEF DESCRIPTION OF THE SEVERAL VIEWS OF THE DRAWING

FIG. 4 is a perspective view of the front of a large square baler hay harvesting and baling apparatus, including another embodiment of the system for measuring the moisture of hay in the pre-compression chamber of the baler of the present invention. This embodiment of the system utilizes a triangular blade sensor.

FIG. 5 is a detailed view of the portion --3-- of FIG. 4.
FIG. 6 is a detailed view of the portion --6-- of FIG. 5.
FIG. 7 is a top view of the large square baler including the moisture measurement system.
FIG. 8 is a detailed view of the portion --8-- of FIG. 7.
FIG. 9 is a detailed view of the portion --9-- of FIG. 8.
FIG. 10 is a front view of the large square baler including the moisture measurement system.
FIG. 11 is a detailed view of the portion --11-- of FIG. 10.
FIG. 12 is a detailed view of the portion --12-- of FIG. 11.

DETAILED DESCRIPTION

Figure 1:
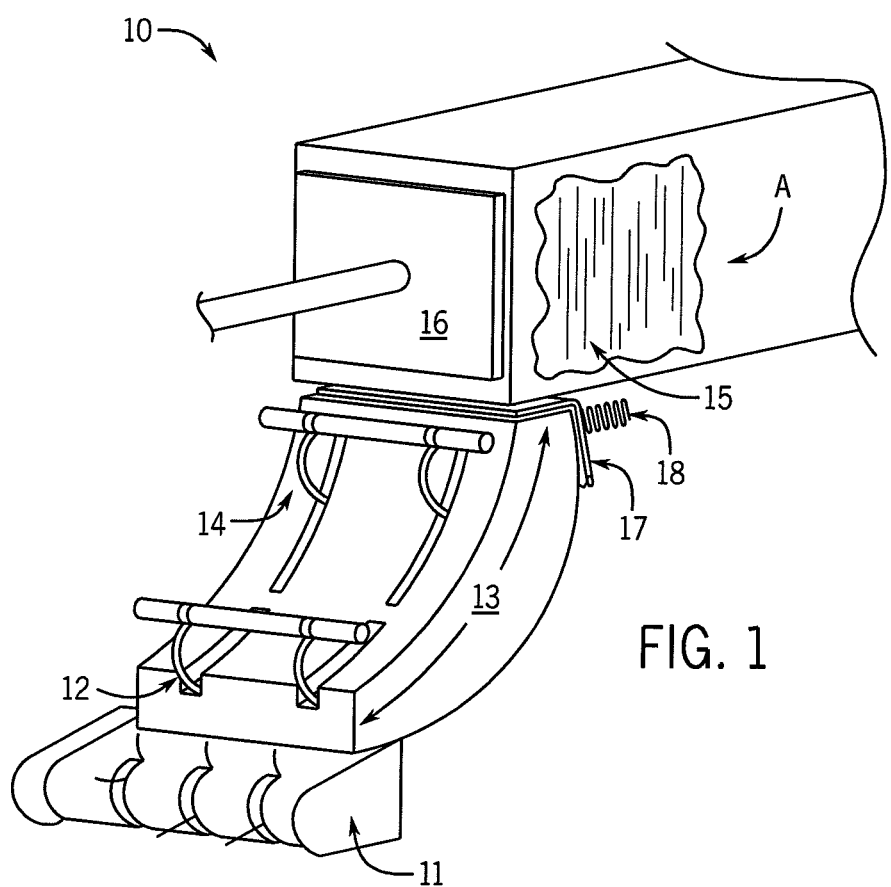
FIG. 1 illustrates an embodiment of the moisture measurement apparatus and method of the present invention in connection with a large square baler, and showing the pre-compression chamber and baler chamber components used to control the density of the material being baled.

A large square baler picks up loose hay from a field and compact it into a transportable rectangular bale. Referring to FIG. 1, the improved large square baler 10 of the present invention includes a pick up mechanism 11, a pre-compression chamber 13, and a bale chamber 15. These components cooperate to pickup loose hay from a field and compact it into a transportable, rectangular bale A.

The sequence of steps of pick up and baling begin with gathering the loose hay with the pick-up device 11, moving the hay from the pick-up with gathering forks 12, compacting the hay in a pre-compression chamber 13 with stuffer arms 14, and compacting the hay in the chamber 15 with a plunger 16. In the device and method of the invention, a pre-compression door 17 is utilized to hold the hay in the pre-compression chamber until the hay has reached a uniform density. The pre-compression door 17 is held in place by a spring 18 or multiple of springs. The stuffer arms 14 continue to increase pressure on the door 17 until the force of the spring 18 is overcome, at which point the door 17 releases the hay in the pre-compression chamber 13 and it is moved by the stuffer arms 14 into the chamber 15. Just before and after the door 17 releases, density of the hay in the pre-compression chamber 13 is similar to each period just before and after the door opens.

Figure 2:
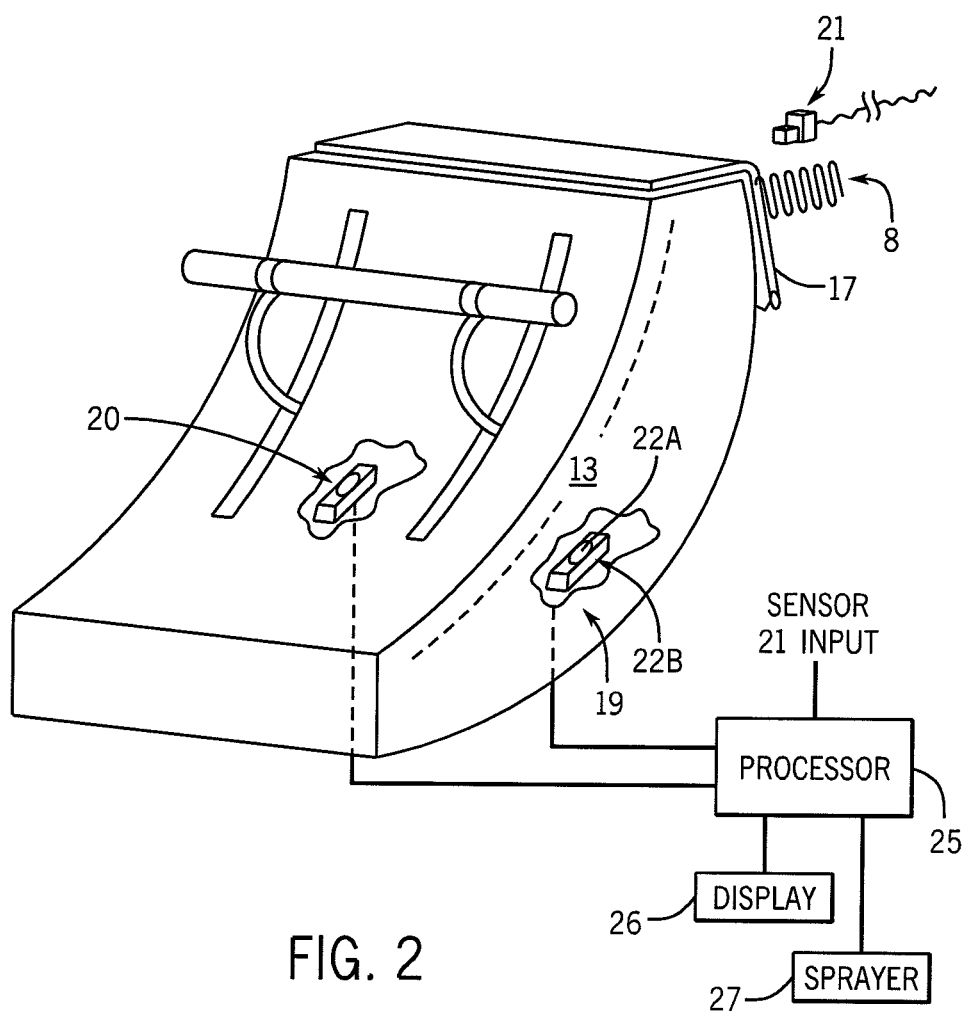
FIG. 2 illustrates the system for measuring hay moisture, including two electrical transmission sensors located inside the pre-compression chamber of the baler of FIG. 1.

Referring also to FIG. 2, the moisture measurement elements of the apparatus 10 include electrical sensors 19 and 20 are mounted to contact the hay in the pre-compression chamber 13. These sensors 19 and 20 may be positive and negative conductivity sensors. Alternatively, they may be senders and receivers of radio wave transmissions. The sensors 19 and 20 are normally paired between one positive and one negative sensor for conductivity readings and one sender and one receiver for radio wave readings. In a further configuration of the invention, there may be multiple pairs or more than one type in a set and transmissions can be added or averaged between multiple pairs or sensors. The sensors 19 and 20 are connected to a processor 25 that takes and records electrical transmission readings at an interval between 3 times per millisecond and one time per second. An independent, door opening sensor 21 is located so that is signals when the door 17 opens. Based on this signal, the processor 25 is programmed to select the values of the transmissions between the sensors 19 and 20 during a period of 0.5 milliseconds to 3 seconds before the door 17 opens and a period of 0.5 milliseconds and 1 second after the door 17 opens. With the normal period of reading between 1.0 milliseconds to 4 seconds, the processor 25 will have between 3 and 400 readings during the read period. To enhance accuracy, these readings are normally averaged by the processor 25 for the period. That average value of electrical transmission can be calibrated to hay moisture and displayed for the operator of the baler 10, written to a bale record, used to calculate yield or control the flow of hay preservative from a dispenser (not shown). In the electrical sensor set shown that use conductivity between at least one positive electrode 19 and at least one negative electrode 20, each sensor is constructed of a conductive material such as metal 22A and isolated from surrounding material by non-conductive material 22B such as plastic. In the alternative embodiment wherein radio wave emissions are used to measure electrical transmissions, one or more sensors 19 emits the radio wave and one or more sensors 20 receives the radio waves.

Figure 3:
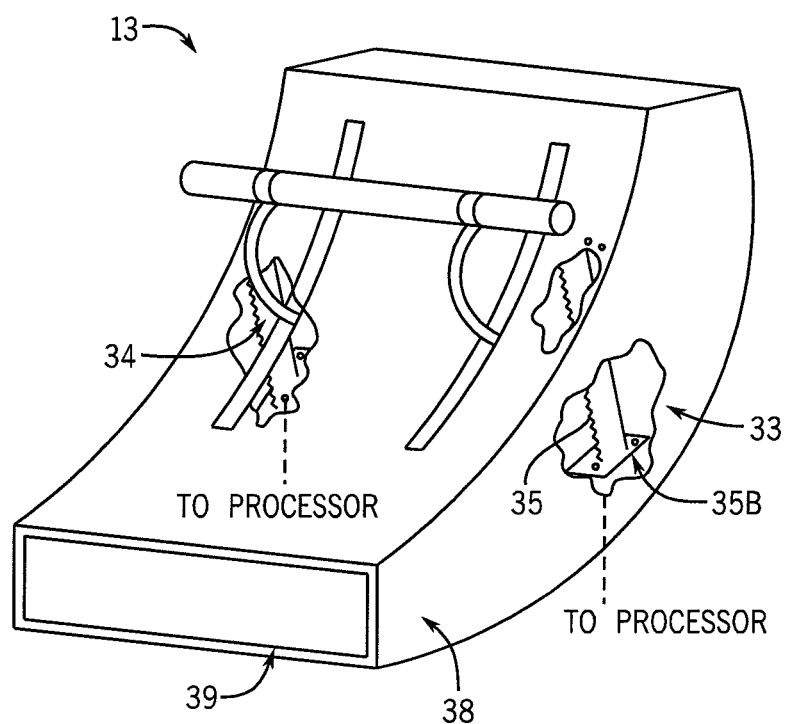
FIG. 3 illustrates an alternative embodiment of sensors of the moisture measurement system, namely two knife-type sensors.
Figure 14:
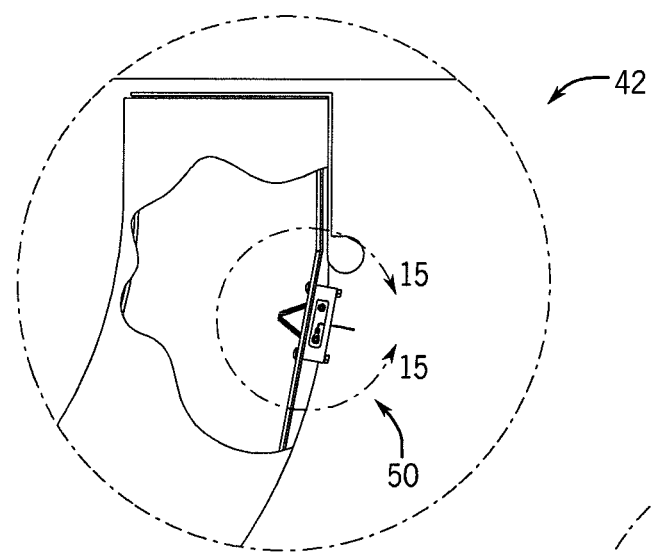
FIG. 14 is a detailed view of the portion --14-- of FIG. 13.
Figure 15:
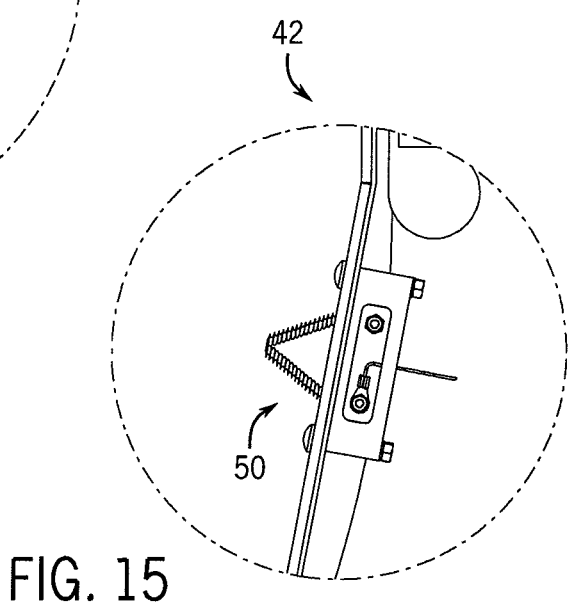
FIG. 15 is a detailed view of the portion --15-- of FIG. 14.
Figure 13:
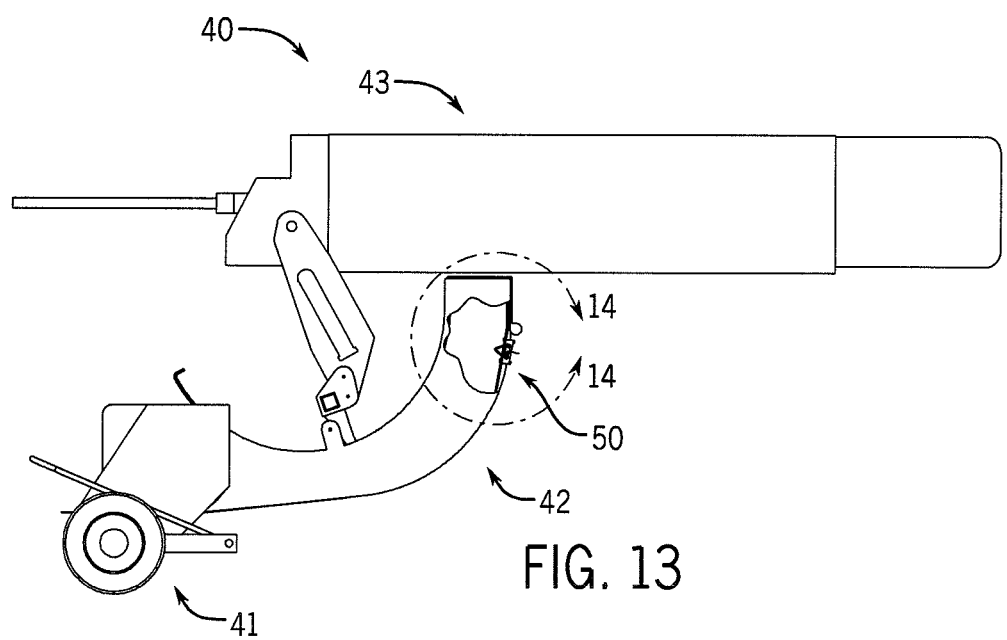
FIG. 13 is a side view of the large square baler including the moisture measurement system.
Figure 17:
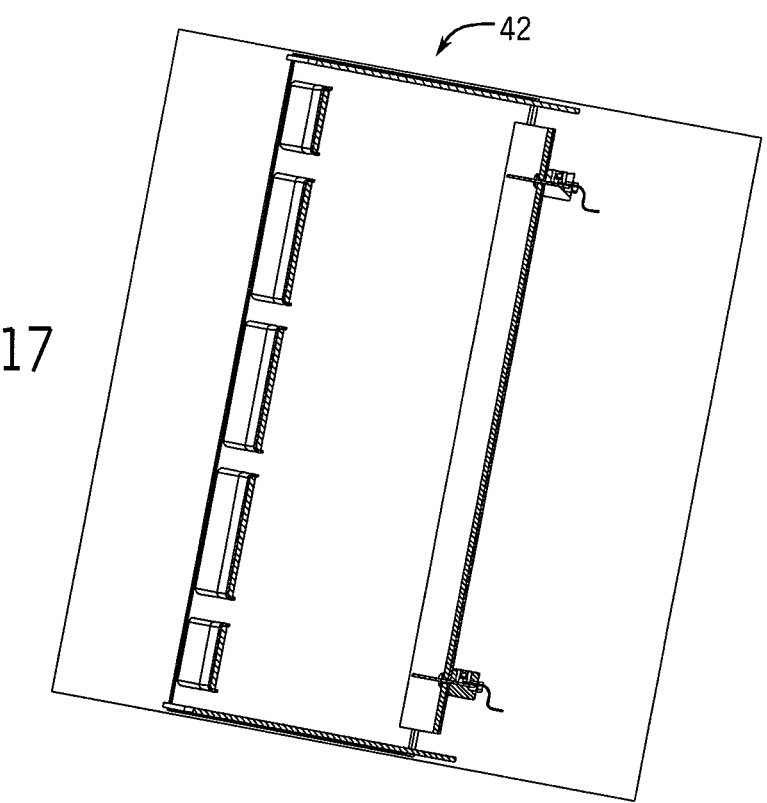
FIG. 17 is a crossectional view of the baler taken along line 17-17 of FIG. 16.
Figure 16:
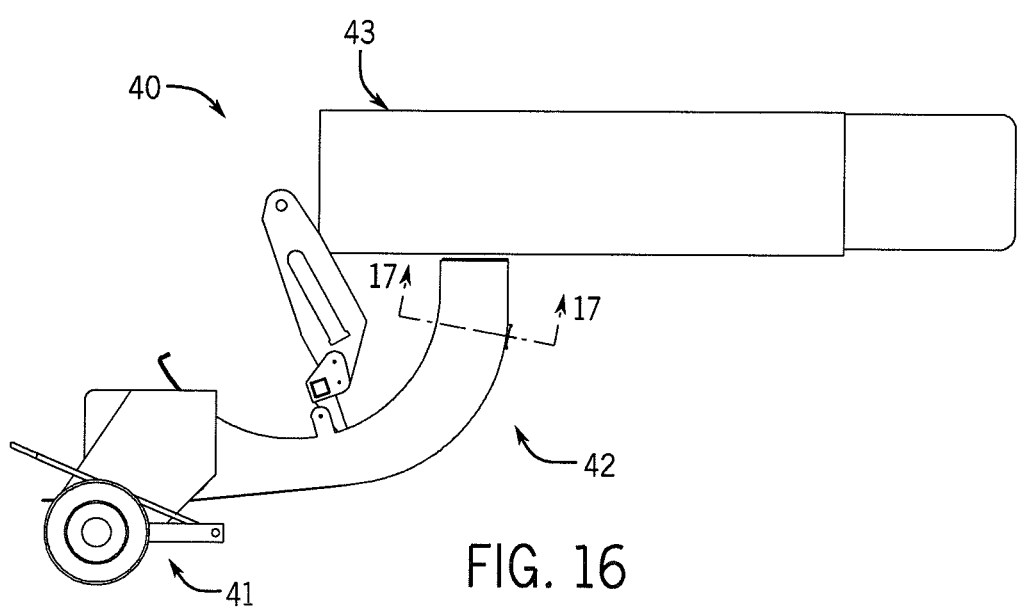
FIG. 16 is another side view of the large square baler including the moisture measurement system.
Figure 18:
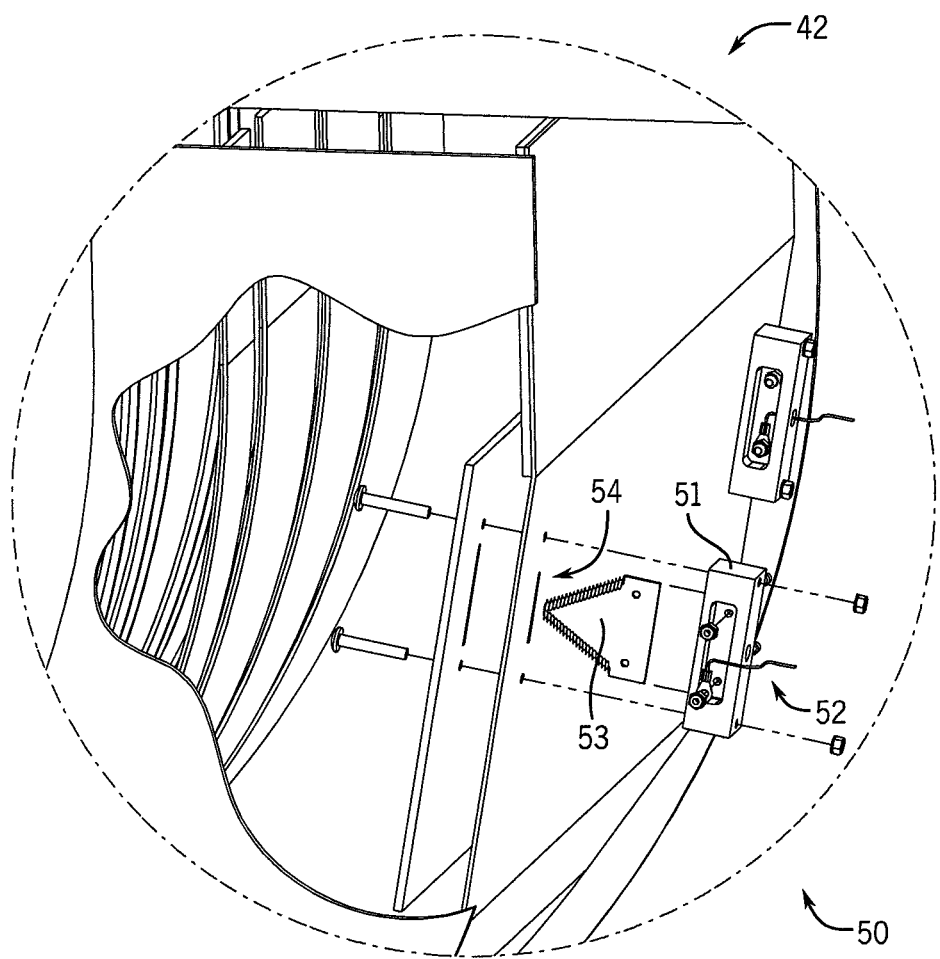
FIG. 18 is an exploded view of components of the moisture measurement system deployed in the pre-compression chamber of the large square baler.
Figure 19:
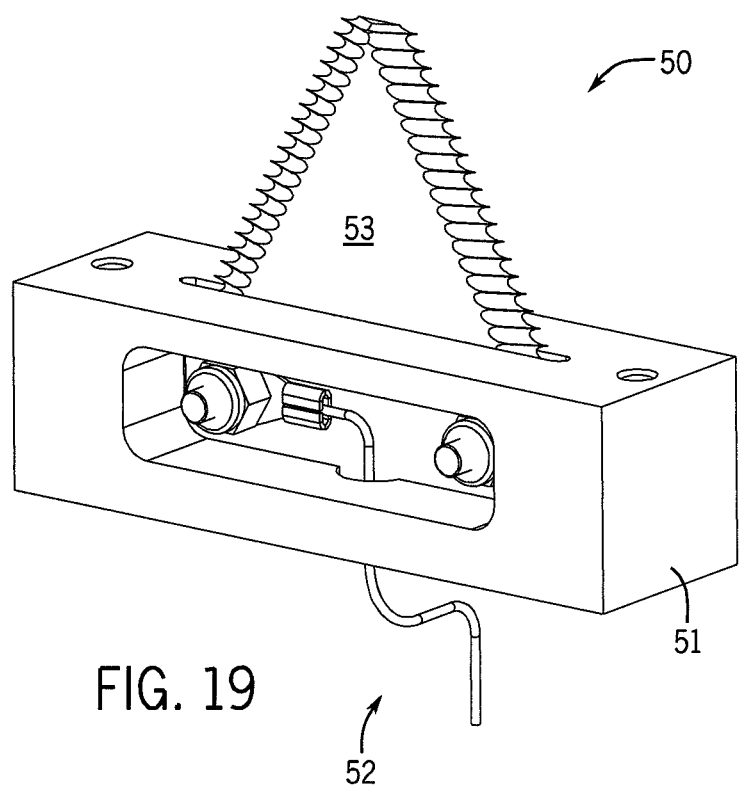
FIG. 19 is a perspective view of an embodiment of a sensor used in the moisture measurement system.
Figure 21:
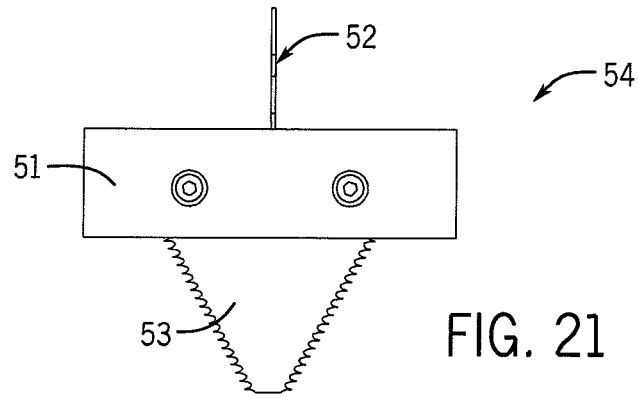
FIG. 21 is a back view of the sensor.
Figure 23:
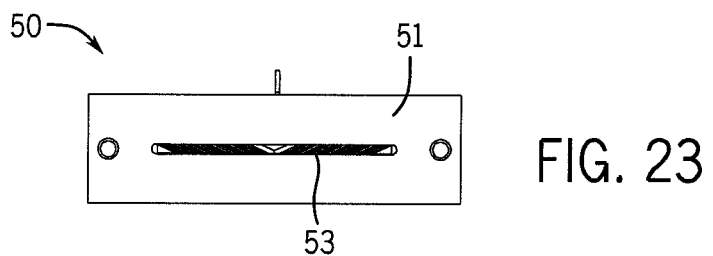
FIG. 23 is a top view of the sensor.
Figures 20, 22, 25:
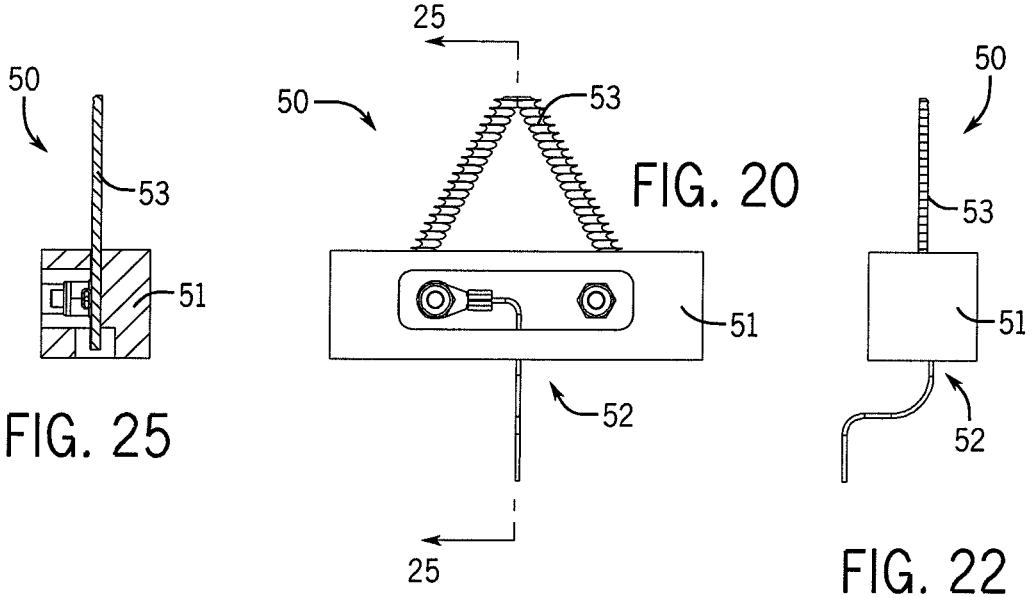
FIG. 20 is a front view of the sensor.
FIG. 22 is an end view of the sensor.
FIG. 25 is a crossectional view of the sensor taken along line 25-25 of FIG. 20.
Figure 24:
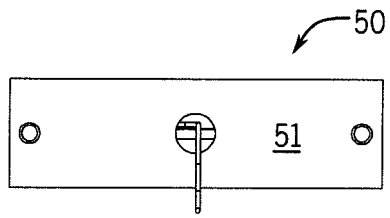
FIG. 24 is a bottom view of the sensor.

FIG. 3 illustrates an alternative embodiment of a sensor of the moisture sensing system. When using conductivity to measure electrical transmission, the nature of the surface of the material being baled that contacts the electrodes is influential in the value of conductivity transmitted from positive electrode to negative electrode. Electrodes that cut the surface of the material such as a stationary knife 33 and 34 create a uniform surface by cutting the hay as it passes by the sensors 33 and 34. In this case the knifes 33 and 34 can be the positive and negative metal electrodes 35A when connected to power and ground and isolated from other conductive material with non-conductive material 35B.

Electrical transmission, conductivity or radio wave (RF), is influenced by conductive surfaces such as metal side wall 38 of the pre-compression chamber 13 that can interrupt or magnify the transmitted electrical signal. To prevent this influence the inside surface of the pre-compression chamber 13 can be lined with a non-conductive material such as plastic 39 so that the conductive material does not influence electrical transmission. This lining technique would be far more difficult due to the increase area of surface to cover in the chamber 15 of the baler.

Returning to FIG. 2, a further alternative embodiment of the invention involves utilizing substantially all of the elements of apparatus 10. In this alternative embodiment however, the independent sensor 11 that senses when the door 17 open is eliminated. In place, the processor 25 continuously monitors the electrical transmission between the sensors 19 and 20 at a frequency between 0.5 milliseconds and 3 seconds. The processor analyzes the data gathered from the continuous monitoring. As the hay in the pre-compression chamber reaches a maximum density before the pre-compression door 17 releases, the electrical transmission between the sensors 19 and 20 will reach a maximum due to the effect of increasing the density of the hay increase the electrical transmission between the sensors. At this point the processor 25 records the maximum electrical transmission.

In yet a further embodiment of the device and method of the invention, the electrical transmission between sensors 19 and 20 is read into the processor 25 which alternatively read individual values of electrical transmission or multiple values that are averaged or processed in some other way pre-programmed into the processor 25. The values of electrical transmission read are converted by the processor 25 to a moisture value by comparing the electrical transmission value to a lookup table in a memory associated with the processor where changes in levels of electrical transmission indicate changes in moisture. The value of moisture from the lookup table can be sent to a display 26, or alternatively used to control other functions such as the application of preservative via a sprayer 27 or other application means.

Figure 27:
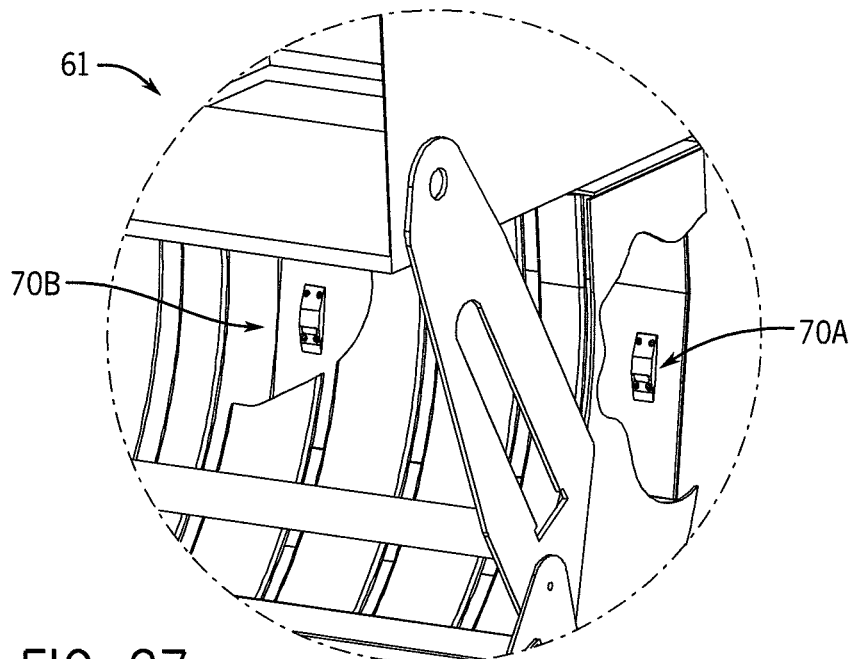
FIG. 27 is a detailed view of portion --27-- of FIG. 26.
Figure 26:
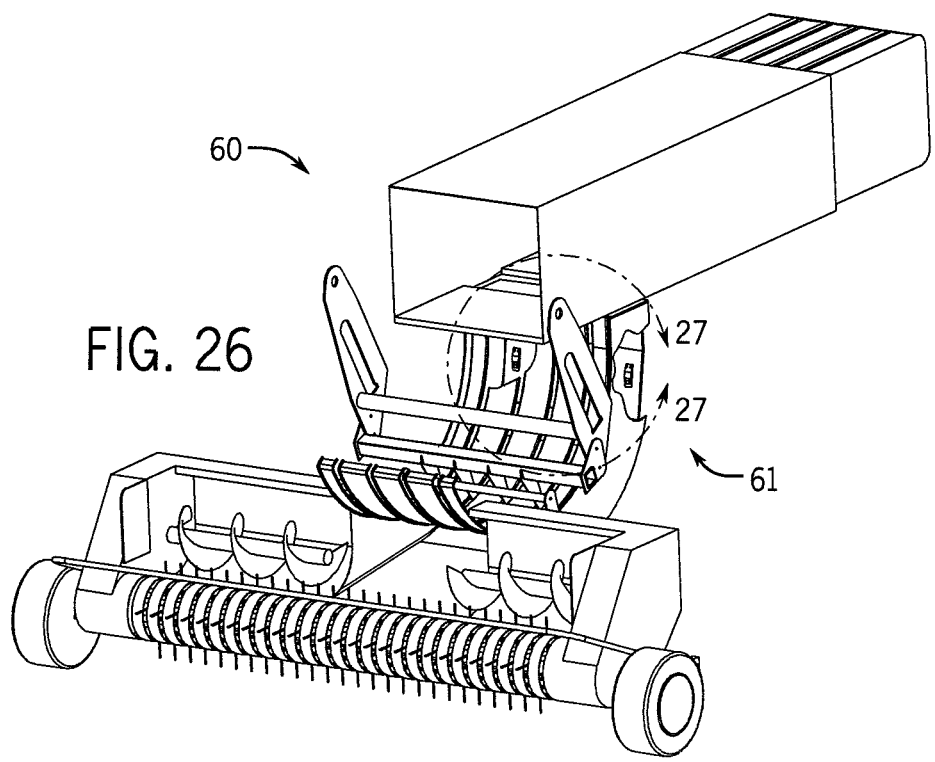
FIG. 26 is a perspective view of the front of a baler including an alternative embodiment of the moisture measurement system of the present invention.
Figure 28:
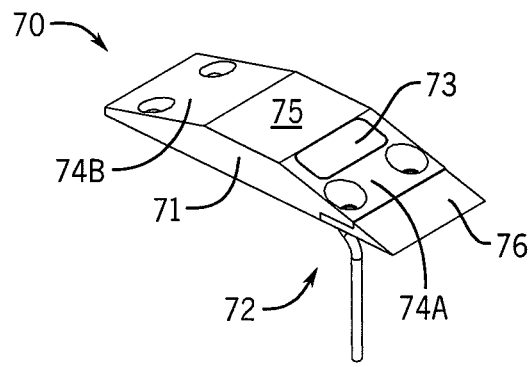
FIG. 28 is a perspective view of an alternative embodiment of the sensor of the system.
Figure 32:
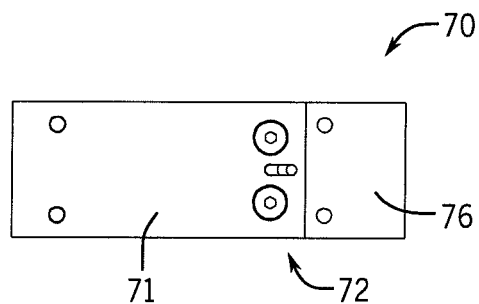
FIG. 32 is a top view of the sensor.
Figure 31:
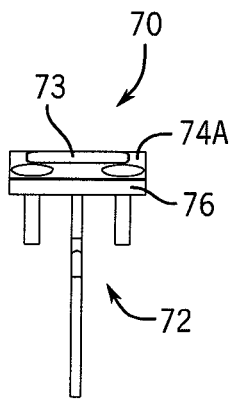
FIG. 31 is an opposite end view of the sensor.
Figure 29:
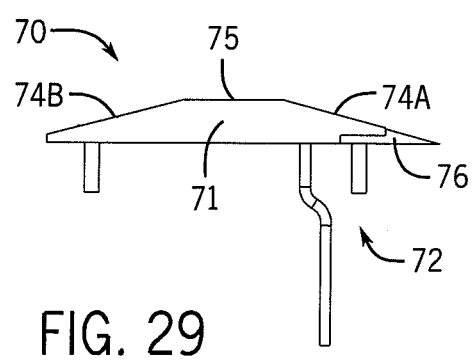
FIG. 29 is a front view of the sensor.
Figure 30:
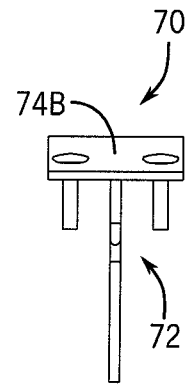
FIG. 30 is an end view of the sensor.
Figure 33:
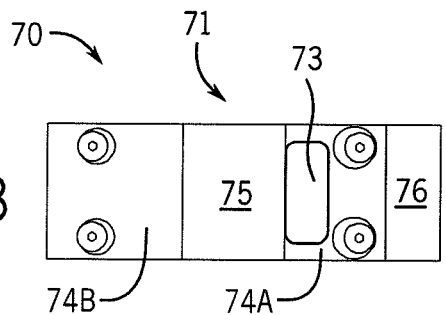
FIG. 33 is a bottom view of the sensor.

FIGS. 4-25 show further embodiment of the moisture measurement system of the invention utilizing at least one pair of triangular blade type sensors 50A and 50B. As is best shown in FIGS. 4, 7, 10, and 13, the system is deployed on a large square hay baler 40 including a pickup unit 41, a pre-compression chamber 42 and a baler chamber 43. Referring also to FIGS. 18-25, the sensor 50 embodiment includes a base member 51, an electrical connection assembly 52, and a blade member 53. The base 51, or a part thereof, is constructed of an electrically non-conductive material so that it insulates the sensor 50 from the conductive surfaces of the pre-compression chamber 42. In this embodiment, the base 51 is connected to the exterior of the wall of the pre-compression chamber 42 at a predetermined point thereon by mounting means. The blade 53 is constructed of an electrically conductive material and has a triangular configuration with cutting means, in this case serrated edges. The blade 53 is connected to the base 51 and extends through a slot 54 in the wall into the pre-compression chamber 42 whereby in use it is exposed for contact with hay moving the pre-compression chamber 42. The electrical connection assembly 52 communicatively connects the blade 53 to the processor (not shown). In this aspect of the invention, the sensors not only sense, but also act as knives that cut the surface of the material being baled FIGS. 26-33 show a still further embodiment of the sensors of the moisture measurement system utilizing at least one pair of side over pad type sensors 70A and 70B. FIGS. 26 and 27 show the sensor 70 disposed on a large square hay baler 60 in the pre-compression chamber 61 thereof. Referring also to FIGS. 28-33, the sensor 70 has a base member 71, an electrical connection assembly 72, and a conductive pad member 73. The base 71, or a part thereof, is constructed of material that is non-conductive to electricity. The base 71 has a rectangular configuration with a tapered top side with ramp surfaces 74A and B and flat top surface 75. The sensor 70 further includes a forward ramp member 76. In this embodiment, the base 71 is connected to the interior of the wall of the pre-compression chamber 61 at a predetermined point thereon by mounting means. The pad 73 is constructed of an electrically conductive material such as a metal. The pad 73 is connected to the base 71 so that in use, it is exposed for contact with hay moving the pre-compression chamber 61. Preferably, the pad 73 is disposed in the forward facing (relative to incoming hay) ramp surface 74A. The electrical connection assembly 72 communicatively connects the pad 73 to the processor (not shown).

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. A crop baler of the type forming square bales and having a pickup mechanism, a pre-compression chamber including a pre-compression door disposed at an output end of the pre-compression chamber and adapted to hold crop in the pre-compression chamber until crop has reached a predetermined density whereupon the door releases crop into a bale chamber, comprising: at least two moisture sensors disposed at separate predetermined positions in the pre-compression chamber, the sensors sensing a parameter associated with moisture of crop disposed in the pre-compression chamber, a processor communicatively connected to the at least two moisture sensors, a door open sensor communicatively connected to the processor for signaling when the door opens, and a display communicatively connected to the processor, wherein the processor configured to calculate, the moisture of crop disposed in the pre-compression chamber from signals from the at least two moisture sensors at a predetermined time period surrounding pre-compression door opening from a signal from the door open sensor, and wherein the display configured to indicate the calculated moisture of the crop so that a user can accurately determine whether to continue or stop baling based on desired crop moisture based on a uniform density of crop in the pre-compression chamber adjacent the pickup mechanism.

2. The crop baler of claim 1, wherein the parameter associated with crop moisture is electrical conductivity, and wherein a first moisture sensor has a positive electrode and wherein a second moisture sensor has a negative electrode.

3. The crop baler of claim 1, wherein the parameter associated with crop moisture is RF Wave transmission, and wherein a first moisture sensor transmits a radio wave and wherein a second moisture sensor receives the radio wave.

4. The crop baler of claim 1, wherein the moisture sensors are disposed at opposite sides of the pre-compression chamber.

5. The crop baler of claim 1, further comprising a lining disposed on a predetermined portion of the pre-compression chamber, the lining being constructed of a material that is non-conductive to electricity.

6. The crop baler of claim 1, wherein the crop is hay.

7. The crop baler of claim 6, wherein the baler is a large square hay baler.

8. The crop baler of claim 1, wherein: (a) the crop is hay, (b) the baler is a large square baler (c) wherein the sensors are disposed on opposite sides of the pre-compression chamber; the crop baler further comprising (d) a hay preservative applicator communicatively connected to the processor.

9. The crop baler of claim 1, wherein the predetermined time period surrounding pre-compression door opening is from 0.5 milliseconds-3.0 seconds before opening to 0.5 milliseconds-10 second after opening.

10. A crop baler of the type forming square bales and having a pickup mechanism, a pre-compression chamber including a pre-compression door disposed at an output end of the pre-compression chamber and adapted to hold crop in the pre-compression chamber until crop has reached a predetermined density whereupon the door releases crop into a bale chamber, comprising: at least two moisture sensors disposed at separate predetermined positions in the pre-compression chamber, the sensors sensing a parameter associated with moisture of crop disposed in the pre-compression chamber, a processor communicatively connected to the at least two moisture sensors, a door open sensor communicatively connected to the processor for signaling when the door opens, and a display communicatively connected to the processor, wherein the processor configured to calculate the moisture of crop disposed in the pre-compression chamber from signals from the at least two moisture sensors by continuously monitoring crop density in the pre-compression chamber at a predetermined frequency, and calculate crop moisture from the continuously monitored data when the crop reaches a maximum density, and wherein the display configured to indicate the calculated moisture of the crop so that a user can accurately determine whether to continue or stop baling based on desired crop moisture based on a uniform density of crop in the pre-compression chamber adjacent the pickup mechanism.

11. The crop baler of claim 10, wherein the predetermined frequency is between 0.5 milliseconds to 3.0 seconds.

12. A crop baler of the type forming square bales and having a pickup mechanism, a pre-compression chamber including a pre-compression door disposed at an output end of the pre-compression chamber and adapted to hold crop in the pre-compression chamber until crop has reached a predetermined density whereupon the door releases crop into a bale chamber, comprising: at least two moisture sensors disposed at separate predetermined positions in the pre-compression chamber, the sensors sensing a parameter associated with moisture of crop disposed in the pre-compression chamber, a processor communicatively connected to the at least two moisture sensors, a door open sensor communicatively connected to the processor for signaling when the door opens, and a display communicatively connected to the processor, wherein the processor configured to calculate the moisture of crop disposed in the pre-compression chamber from signals from the at least two moisture sensors by (i) reading signals, (ii) averaging the signals, and (iii) converting the signal values to a moisture value by comparing them to a lookup table, and calculate crop moisture based on a comparison of the signals to the lookup table values, and wherein the display configured to indicate the calculated moisture of the crop so that a user can accurately determine whether to continue or stop baling based on desired crop moisture based on a uniform density of crop in the pre-compression chamber adjacent the pickup mechanism.

* * * * *